(12) United States Patent
Ahlers et al.

(10) Patent No.: US 6,977,312 B2
(45) Date of Patent: Dec. 20, 2005

(54) PHOSPHOR, ARSENIC AND ANTIMONY COMPOUNDS BASED UPON DIARYL-ANELLATED BICYCLO[2.2.N] PARENT SUBSTANCES AND CATALYSTS CONTAINING SAME

(75) Inventors: Wolfgang Ahlers, Worms (DE);
Michael Röper, Wachenheim (DE);
Peter Hofmann, Heidelberg (DE);
Daniel C. M. Warth, Heidelberg (DE);
Rocco Paciello, Bad Dürkheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/203,296

(22) PCT Filed: Feb. 9, 2001

(86) PCT No.: PCT/EP01/01422
§ 371 (c)(1),
(2), (4) Date: Aug. 8, 2002

(87) PCT Pub. No.: WO01/58589
PCT Pub. Date: Aug. 16, 2001

(65) Prior Publication Data
US 2003/0055253 A1 Mar. 20, 2003

(30) Foreign Application Priority Data
Feb. 10, 2000 (DE) .......................... 100 05 794
Oct. 23, 2000 (DE) .......................... 100 52 462

(51) Int. Cl.$^7$ ................................ C07F 9/02
(52) U.S. Cl. ..................... 568/17; 568/13; 568/14; 568/15; 556/7; 556/70; 556/76; 548/402; 548/3; 548/4; 546/2
(58) Field of Search ................ 568/17, 13, 14, 568/15; 548/402; 556/7, 70, 76, 64; 546/2; 549/3, 4

(56) References Cited

U.S. PATENT DOCUMENTS
5,874,629 A * 2/1999 Pye et al. ................ 568/17
6,290,926 B1    9/2001 Haenel et al.
6,333,291 B1 * 12/2001 Yokozawa et al. ........ 502/162

FOREIGN PATENT DOCUMENTS
| WO | 98/30569 | 7/1998 |
|---|---|---|
| WO | 98/39345 | 9/1998 |
| WO | 02/083695 | 10/2002 |

OTHER PUBLICATIONS
Fu et al., Tetrahedron Letters, 1994, 35 (41), 7593–7596 {The synthesis of anthraphos, a conformationally rigid, C2 symmetric diphosphine and the x-ray crystal structure of [Rh(COD)(anthraphos)]BF4.*
CA:128:230464 abs of Synlett by Haenel et al (3) pp 301–303 1998.*
CA:114:102349 abs of Chemisch Berichte by Haenel 124(2) pp 333–336 1991.*
CA:136:118494 abs of Chemical Society of Japan by Yamashita et al (110) pp 104–105 2001.*
J.MOL. Cat. A:014(1995)17–85, Beller et al.
Tet.Ltr,Band,34,Nr. 13, 2107ff(1993,Haenel et al.
Organometallics 1984,3,33ff,Tolman et al.
Advances in Catalysis,vol. 33, 1985,1ff.
XP–002170785 Derwent Abst.
Tet.Ltr.,39,(1998)813–816.
Tet.Ltr.,vol. 36,No.75ff(1995), Haenel et al.
Chem.Ber. 124, 1705ff(1991), Haenel et al.
Organometallics 1995,14, 3081, Van Leeuwen et al.
OZ 52364 = WO 02/083695.

* cited by examiner

*Primary Examiner*—Joann Richter
*Assistant Examiner*—Chukwuma Nwaonicha
(74) *Attorney, Agent, or Firm*—Novak Druce & Quigg

(57) ABSTRACT

Novel compounds of phosphorus, of arsenic and of antimony can be used as ligands to form complexes of metals of transition group VIII which can be used in catalysts for hydroformylation, hydrocyanation, carbonylation, hydrogenations, oligomerization and polymerization of olefins and for metathesis.

18 Claims, No Drawings

PHOSPHOR, ARSENIC AND ANTIMONY COMPOUNDS BASED UPON DIARYL-ANELLATED BICYCLO[2.2.N] PARENT SUBSTANCES AND CATALYSTS CONTAINING SAME

The present invention relates to compounds of phosphorus, of arsenic and of antimony, to a process for preparing them and to a catalyst comprising at least one complex of a metal of transition group VIII with such a compound as ligand. The invention further relates to the use of these catalysts for hydroformylation, hydrocyanation, carbonylation, hydrogenation, olefin oligomerization and olefin polymerization and for metathesis.

Hydroformylation or the oxo process is an important industrial process employed for preparing aldehydes from olefins, carbon monoxide and hydrogen. These aldehydes can, if desired in the same process step, be hydrogenated by means of hydrogen to form the corresponding oxo alcohols. The reaction itself is strongly exothermic and generally proceeds under superatmospheric pressure at elevated temperatures in the presence of catalysts. Catalysts used are Co, Rh, Ir, Ru, Pd or Pt compounds or complexes which may be modified by N- or P-containing ligands to influence the activity and/or selectivity. The hydroformylation reaction results in formation of mixtures of isomeric aldehydes because CO can add onto either of the two carbon atoms of a double bond. In addition, double bond isomerization can also occur. In these isomeric mixtures, the n-aldehyde frequently predominates over the isoaldehyde and, owing to the significantly greater industrial importance of the n-aldehydes, optimization of the hydroformylation catalysts to achieve a greater n-selectivity is sought.

It is known that phosphorus-costaining ligands can be used in the low-pressure rhodium-catalyzed hydroformylation to stabilize and/or activate the catalyst metal. Examples of suitable phosphorus-containing ligands are phosphines, phosphinites, phosphonites, phosphites, phosphoramidites, phospholes and phosphabenzenes. The most widespread ligands at present are triarylphosphines, e.g. triphenylphosphine and sulfonated triphenylphosphine, since these have sufficient stability under the reaction conditions. However, these ligands have the disadvantage that, in general, only very high ligand excesses give satisfactory yields, in particular of linear aldehydes. On the other hand, chelating phosphites give high yields of linear aldehydes even at generally very low ligand excesses, but these ligands have the disadvantage of a low stability which, combined with their relatively high acquisition costs, has an adverse effect on the economics of the hydroformylation process.

Beller et al., Journal of Molecular Catalysis A, 104 (1995), pages 17–85, describe rhodium-containing, phosphine-modified catalysts for the hydroformylation of low-boiling olefins.

DE-A-196 523 50 describes catalysts based on 4,5-diphosphinoacridine ligands. These are suitable for catalyzing carbon monoxide converting by means of the water gas equilibrium. Furthermore, they are said to be suitable for catalyzing hydroformylation, carbonylation, carboxylation, hydrogenation, hydrocyanation, hydrosilylation, polymerization, isomerization, cross coupling and metathesis. The latter is not evidenced by examples in the document. Disadvantages of these ligands are their complicated multistage synthesis and the angle of bite which is unfavorable for chelating rhodium.

In Tetrahedron Letters, volume 34, No. 13, pages 2107ff (1993), in Tetrahedron Letters, volume 36, No. 1, pages 75ff (1995) and in Chem. Ber. 124, page 1705ff (1991), Haenel et al. describe the synthesis of bis(diphenylphosphino) chelates based on anthracene, dibenzofuran, dibenzothiophene and xanthene parent molecules. The use of these compounds in catalysis is not described. Disadvantages of these compounds are their multistage synthesis and, once again, the angle of bite which is unfavorable for chelating rhodium.

In Organometallics 1995, 14, page 3081ff, van Leeuwen et al. describe the synthesis of chelating phosphines based on xanthene as parent molecule and their use as cocatalysts in the low-pressure rhodium-catalyzed hydroformylation of α-olefins. Disadvantages of these ligands are the complicated synthesis of the parent xanthene structure and the necessity of using sensitive organometallic compounds in the synthesis. Hydroformylation processes using catalysts on the basis of these ligands are therefore economically disadvantageous.

The catalytic hydrocyanation of olefins for the preparation of nitriles likewise has great industrial importance.

"Applied Homogeneous Catalysis with Organometallic Compounds", volume 1, VCH Weinheim, page 465ff, describes the heterogeneously and homogeneously catalyzed addition of hydrogen cyanide onto olefins in general terms. Catalysts used are, in particular, catalysts based on phosphine, phosphite and phosphonite complexes of nickel and palladium.

In Organometallics 1984, 3, page 33ff, C. A. Tolman et al. describe the catalytic hydrocyanation of olefins in the presence of nickel(0) phosphite complexes taking specific account of the effect of Lewis acids on the hydrogen cyanide addition.

Advances in Catalysis, volume 33, 1985, Academic Press Inc., page 1ff, gives an overview of the homogeneously nickel-catalyzed hydrocyanation of olefins. Catalysts used are nickel(0) complexes having phosphine and phosphite ligands.

None of the abovementioned literature references describes catalysts, for example hydroformylation catalysts or hydrocyanation catalysts, based on phosphorus-containing diaryl-fused bicyclo[2.2.n] structures.

It is an object of the present invention to provide new compounds of phosphorus, of arsenic and of antimony and also a process for preparing them. These compounds should preferably be suitable as ligands for transition metal complexes of metals of transition group VIII so as to provide novel catalysts based on these metal complexes. These ligands should preferably be easy to prepare and/or their complexes should be very stable under the reaction conditions of the reactions to be catalyzed. The catalysts should preferably be suitable for hydroformylation, hydrocyanation or carbonylation and have a good catalytic activity.

We have found that this object is achieved by compounds of phosphorus, of arsenic and of antimony based on diaryl-fused bicyclo[2.2.n] structures which are suitable as ligands for transition metal complexes of metals of transition group VIII.

The present invention accordingly provides compounds of the formula I

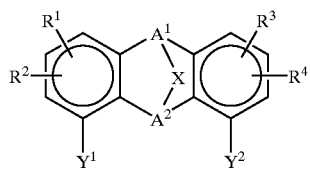

(I)

where
A¹ and A² are each, independently of one another, B, N, P or CR⁵, where R⁵ is hydrogen, alkyl, cycloalkyl, aryl or heteroaryl,
X is O, S, NR$^a$ or a divalent bridging group, where R$^a$ is hydrogen, alkyl, cycloalkyl or aryl,
Y¹ and Y² are, independently of one another, radicals containing at least one phosphorus, arsenic or antimony atom, where the phosphorus, arsenic or antimony atom is bound directly or via an oxygen atom to the phenyl ring in formula I,
R¹, R², R³ and R⁴ are each, independently of one another, hydrogen, alkyl, cycloalkyl, aryl, alkoxy, halogen, NE¹E², alkylene-NE¹E², trifluoromethyl, nitro, alkoxycarbonyl or cyano, where E¹ and E² are identical or different and are each alkyl, cycloalkyl or aryl.

For the purposes of the present invention, the expression 'alkyl' encompasses both straight-chain and branched alkyl groups. Preference is given to straight-chain or branched $C_1$–$C_8$-alkyl groups, more preferably $C_1$–$C_6$-alkyl groups and particularly preferably $C_1$–$C_4$-alkyl groups. Examples of alkyl groups are, in particular, methyl, ethyl, propyl, isopropyl, n-butyl, 2-butyl, sec-butyl, tert-butyl, n-pentyl, 2-pentyl, 2-methylbutyl, 3-methylbutyl, 1,2-dimethylpropyl, 1,1-dimethylpropyl, 2,2-dimethylpropyl, 1-ethylpropyl, n-hexyl, 2-hexyl, 2-methylpentyl, 3-methylpentyl, 4-methylpentyl, 1,2-dimethylbutyl, 1,3-dimethylbutyl, 2,3-dimethylbutyl, 1,1-dimethylbutyl, 2,2-dimethylbutyl, 3,3-dimethylbutyl, 1,1,2-trimethylpropyl, 1,2,2-trimethylpropyl, 1-ethylbutyl, 2-ethylbutyl, 1-ethyl-2-methylpropyl, n-heptyl, 2-heptyl, 3-heptyl, 2-ethylpentyl, 1-propylbutyl, octyl.

Cycloalkyl is preferably a $C_5$–$C_7$-cycloalkyl group such as cyclopentyl, cyclohexyl or cycloheptyl.

If the cycloalkyl group is substituted, it preferably has 1, 2, 3, 4 or 5, in particular 1, 2 or 3, substituents selected from among alkyl, alkoxy and halogen.

Aryl is preferably phenyl, tolyl, xylyl, mesityl, naphthyl, anthracenyl, phenanthrenyl or naphthacenyl, in particular phenyl or naphthyl.

Substituted aryl radicals preferably have 1, 2, 3, 4 or 5, in particular 1, 2 or 3, substituents selected from among alkyl, alkoxy, carboxyl, carboxylate, trifluoromethyl, —SO₃H, sulfonate, NE¹E², alkylene-NE¹E², nitro, cyano and halogen. A preferred substituted aryl radical is pentafluorophenyl.

Heteroaryl is preferably pyrrolyl, pyrazolyl, imidazolyl, indolyl, carbazolyl, pyridyl, quinolinyl, acridinyl, pyridazinyl, pyrimidinyl or pyrazinyl.

Substituted heteroaryl radicals preferably have 1, 2 or 3 substituents selected from among alkyl, alkoxy, —SO₃H, sulfonate, NE¹E², alkylene-NE¹E², trifluoromethyl and halogen.

What has been said above regarding alkyl, cycloalkyl and aryl radicals applies analogously to alkoxy, cycloalkyloxy and aryloxy radicals.

The groups NE¹E² are preferably N,N-dimethylamino, N,N-diethylamino, N,N-dipropylamino, N,N-diisopropylamino, N,N-di-n-butylamino, N,N-di-t-butylamino, N,N-dicyclohexylamino or N,N-diphenylamino.

Halogen is fluorine, chlorine, bromine or iodine, preferably fluorine, chlorine and bromine.

For the purposes of the present invention, carboxylate is preferably a derivative of a carboxylic acid function, in particular a metal carboxylate, a carboxylic ester function or a carboxamide function, particularly preferably a carboxylic ester function. These include, for example, esters of $C_1$–$C_4$-alkanols such as methanol, ethanol, n-propanol, isopropanol, n-butanol, sec-butanol or tert-butanol.

A¹ and A² are preferably selected from among N and CR⁵. If R⁵ is alkyl, cycloalkyl, aryl or hetaryl, these radicals can have at least one substituent. Preferred substituents of the radicals R⁵ are polar (hydrophilic) groups. The polar groups are preferably selected from among COOR$^k$, COO⁻M⁺, SO₃R$^k$, SO₃⁻M⁺, NE³E⁴, NE³E⁴E⁵⁺X⁻, OR$^f$, SR$^f$, (CHR¹CH₂O)$_x$R$^k$ and (CH₂CH₂N(E³))$_x$R$^k$, where R$^k$, E³, E⁴ and E⁵ are each identical or different radicals selected from among hydrogen, alkyl, cycloalkyl and aryl; R¹ is hydrogen, methyl or ethyl; M⁺ is a cation such as Li⁺, Na⁺, K⁺, NH₄⁺; X⁻ is an anion such as Cl⁻ or Br⁻, and X is an integer from 1 to 120.

If R⁵ is a polymeric support which may be bound via a spacer group, then the support is preferably selected from among styrene homopolymers and copolymers, in particular styrene-divinylbenzene copolymers (Merrifield resins), polyamides, aminomethylated polystyrene resins, etc. Suitable spacers include alkylene chains which maybe interrupted by one or more nonadjacent heteroatoms such as O, S, NR$^x$, where R$^x$ is hydrogen, alkyl, cycloalkyl or aryl. The alkylene chains may also bear functional groups such as ester and/or amino groups.

In a preferred embodiment, R⁵ is hydrogen or substituted or unsubstituted $C_1$–$C_8$-alkyl.

Y¹ and Y² are preferably radicals containing a phosphorus atom, in particular radicals of the formulae PR⁶R⁷, P(OR⁶)R⁷, P(OR⁶)(OR⁷), OPR⁶R⁷, OP(OR⁶)R⁷ and OP(OR⁶)(OR⁷), where
R⁶ and R⁷ are each, independently of one another, alkyl, cycloalkyl, aryl or heteroaryl which may bear one, two or three substituents selected from among alkyl, cycloalkyl, aryl, alkoxy, cycloalkyloxy, aryloxy, halogen, trifluoromethyl, nitro, cyano, carboxyl, carboxylate, acyl, —SO₃H, sulfonate, NE¹E² and alkylene-NE¹E², where E¹ end E² are identical or different and are selected from among alkyl, cycloalkyl and aryl, or
R⁶ and R⁷ together with the phosphorus atom and, if present, the oxygen atom(s) to which they are bound form a 5- to 8-membered heterocycle which may additionally be fused with one, two or three cycloalkyl, aryl and/or heteroaryl rings, where the fused-on groups may each bear, independently of one another, one, two, three or four substituents selected from among alkyl, alkoxy, halogen, nitro, cyano, carboxyl carboxylate and —SO₃H, sulfonate, NE¹E² and alkylene-NE¹E² and where the heterocycle may additionally contain one or two heteroatoms(s) selected from among N, O and S.

The bridging group X is preferably a divalent bridging group having from 1 to 15 atoms in the chain between the flanking bonds.

X is preferably a $C_1$–$C_{10}$-alkylene bridge which may contain one, two, three or four double bonds and/or may bear one, two, three or four substituents selected from among alkyl, alkoxy, halogen, nitro, cyano, carboxyl, carboxylate, cycloalkyl and aryl, where the aryl substituent may additionally bear one, two or three substituents selected from among alkyl, alkoxy, halogen, trifluoromethyl, —SO$_3$H, sulfonate, NE$^1$E$^2$, alkylene-NE$^1$E$^2$, nitro, alkoxycarbonyl and cyano, and/or the alkylene bridge X may be interrupted by one, two or three nonadjacent, substituted or unsubstituted heteroatoms, and/or the alkylene bridge X may be fused with one, two or three aryl and/or heteroaryl rings, where the fused-on aryl and heteroaryl groups may each bear one, two or three substituents selected from among alkyl, cycloalkyl, aryl, alkoxy, cycloalkoxy, aryloxy, acyl, halogen, trifluoromethyl, —SO$_3$H, sulfonate, nitro, cyano, carboxyl, alkoxycarbonyl, NE$^1$E$^2$ and alkylene-NE$^1$E$^2$, where E$^1$ and E$^2$ may be identical or different and are each alkyl, cycloalkyl or aryl.

The radical X is particularly preferably a C$_1$–C$_8$-alkylene bridge which, depending on the number of carbon atoms, is fused with 1, 2 or 3 aryl rings and/or can have 1, 2, 3 or 4 substituents selected from among alkyl, cycloalkyl and substituted or unsubstituted aryl, and/or can additionally be interrupted by 1, 2 or 3 unsubstituted or substituted heteroatoms.

The fused-on aryls of the radicals X are preferably benzene or naphthalene, in particular benzene. Fused-on benzene rings are preferably unsubstituted or have 1, 2 or 3, in particular 1 or 2, substituents selected from among alkyl, alkoxy, halogen, SO$_3$H, sulfonate, NE$^1$E$^2$, alkylene-NE$^1$E$^2$, trifluoromethyl, nitro, carboxyl, alkoxycarbonyl and cyano. Fused-on naphthalenes are preferably unsubstituted or have, in the ring which is not fused-on and/or in the fused-on ring, in each case 1, 2 or 3, in particular 1 or 2, of the substituents specified above for the fused-on benzene rings. These substituents are then preferably alkyl or alkoxycarbonyl. Alkyl as substituent on the fused-on aryls is preferably C$_1$–C$_4$-alkyl and in particular methyl, isopropyl or tert-butyl. Alkoxy is preferably C$_1$–C$_4$-alkoxy and in particular methoxy. Alkoxycarbonyl is preferably C$_1$–C$_4$-alkoxycarbonyl. Halogen is particularly preferably fluorine or chlorine.

If the alkylene bridge of the radical X is interrupted by 1, 2 or 3 unsubstituted or substituted heteroatoms, the heteroatoms are preferably selected from among O, S and NR$^{17}$, where R$^{17}$ is alkyl, cycloalkyl or Aryl.

If the alkylene bridge of the radical X is substituted, it has 1, 2, 3 or 4 substituents which is/are preferably selected from among alkyl, cycloalkyl and aryl, where the aryl substituent may additionally bear 1, 2 or 3 substituents selected from among alkyl, alkoxy, halogen, —SO$_3$H, sulfonate, NE$^1$E$^2$, alkylene-NE$^1$E$^2$, trifluoromethyl, nitro, alkoxycarbonyl and cyano. The substituents of the alkylene bridge X are preferably selected from among methyl, ethyl, n-propyl, isopropyl, n-butyl, sec-butyl, tert-butyl, phenyl, p-(C$_1$–C$_4$-alkyl)phenyl, preferably p-methylphenyl, p-(C$_1$–C$_4$-alkoxy) phenyl, preferably p-methoxyphenyl, p-halophenyl, preferably p-chlorophenyl, and p-trifluoromethylphenyl.

In a preferred embodiment, X is a nonfused C$_1$–C$_3$-alkylene bridge, where C$_2$- and C$_3$-alkylene bridges may contain a double bond. In particular, the radicals X have 1, 2, 3 or 4 substituents selected from among methyl, ethyl, n-propyl, iso-propyl, n-butyl, sec-butyl, tert-butyl, halogen and alkyloxycarbonyl.

In a further preferred embodiment, X is selected from among radicals of the formulae II.1 to II.10

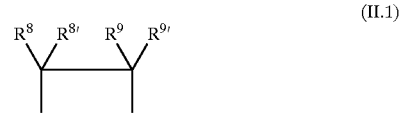
(II.1)

(II.2)

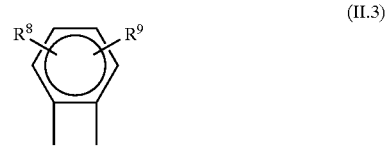
(II.3)

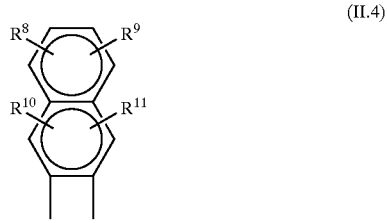
(II.4)

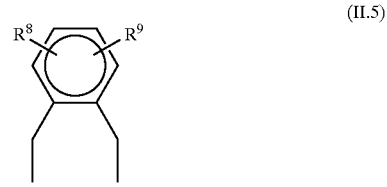
(II.5)

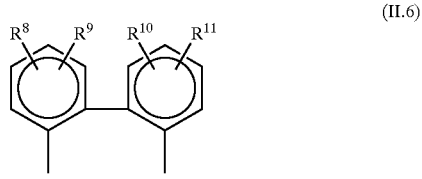
(II.6)

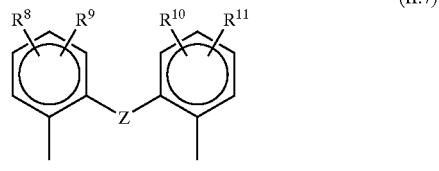
(II.7)

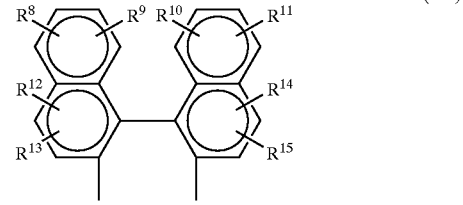
(II.8)

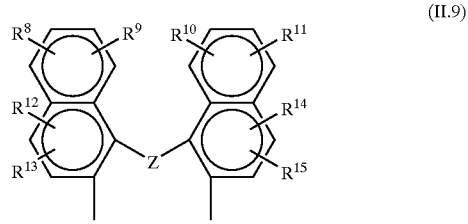
(II.9)

(II.10)

where
Z is O, S or NR$^{16}$, where
  R$^{16}$ is alkyl, cycloalkyl or aryl,
  or Z is a C$_1$–C$_3$-alkylene bridge which may contain a double bond and/or bear an alkyl, cycloalkyl or aryl substituent, where the aryl substituent may bear one, two or three substituents specified for aryl,
  or Z is a C$_2$–C$_3$-alkylene bridge which is interrupted by O, S or NR$^{16}$,
R$^8$, R$^{8'}$, R$^9$, R$^{9'}$, R$^{10}$, R$^{11}$, R$^{12}$, R$^{13}$, R$^{14}$ and R$^{15}$ are each, independently of one another, hydrogen, alkyl, cycloalkyl, aryl, alkoxy, halogen, SO$_3$H, sulfonate, NE$^1$E$^2$, alkylene-NE$^1$E$^2$, trifluoromethyl, nitro, alkoxycarbonyl, carboxyl or cyano.

X is preferably a radical of the formulae II.1 or II.2, where R$^8$ and R$^9$ are, independently of one another hydrogen or C$_1$–C$_4$-alkoxycarbonyl, in particular COOEt. Particularly preferably, R$^8$ and R$^9$ are both hydrogen.

X is preferably a radical of the formula II.3, where R$^8$ and R$^9$ are, independently of one another, hydrogen or C$_1$–C$_4$-alkyl.

In the formula I, it is preferred that one of the radicals Y$^1$ and Y$^2$ or both the radicals Y$^1$ and Y$^2$ are selected from among radicals of the formulae PR$^6$R$^7$, P(OR$^6$)R$^7$, P(OR$^6$)(OR$^7$), OPR$^6$R$^7$, OP(OR$^6$)R$^7$ and OP(OR$^6$)(OR$^7$) in which R$^6$ and R$^7$ are selected from among C$_1$–C$_6$-alkyl, in particular ethyl, n-propyl, isopropyl and tert-butyl, C$_5$–C$_7$-cycloalkyl, in particular cyclohexyl, aryl, in particular phenyl and hetaryl, in particular pyrrolyl, pyrazolyl, imidazolyl, indolyl and carbazolyl.

In the formula I, preference is given to one of the radicals Y$^1$ or Y$^2$ or both radicals Y$^1$ and Y$^2$ being selected from among radicals of the formulae PR$^6$R$^7$, P(OR$^6$)R$^7$, P(OR$^6$)(OR$^7$), OPR$^6$R$^7$, OP(OR$^6$)R$^7$ and OP(OR$^6$)(OR$^7$), where R$^6$ and R$^7$ together with the phosphorus atom and, if present, the oxygen atom(s) to which they are bound form a 5- to 8-membered heterocycle which may additionally be fused with one, two or three cycloalkyl, aryl and/or heteroaryl rings, where the fused-on groups may each bear, independently of one another, one, two, three or four substituents selected from among alkyl, alkoxy, halogen, nitro, cyano, carboxyl, SO$_3$H, sulfonate, NE$^1$E$^2$, alkylene-NE$^1$E$^2$ and carboxylate.

The radicals Y$^1$ and Y$^2$ are preferably selected from among phosphine, phosphinite, phosphonite and/or phosphite groups of the formula III

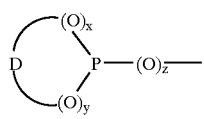
(III)

where
x, y and z are each, independently of one another, 0 or 1 and D together with the phosphorus atom and, if x and/or y are 1, the oxygen atom(s) to which it is bound forms a 5- to 8-membered heterocycle which may additionally be fused with one, two or three cycloalkyl, aryl and/or heteroaryl rings, where the fused-on groups may each bear, independently of one another, one, two, three or four substituents selected from among alkyl, alkoxy, halogen, SO$_3$H, sulfonate, NE$^1$E$^2$, alkylene-NE$^1$E$^2$, nitro, cyano, carboxyl and carboxylate.

The radical D is preferably a C$_2$–C$_7$-alkylene bridge which is fused with 1, 2 or 3 aryl rings and may additionally bear a substituent selected from among alkyl, cycloalkyl and substituted or unsubstituted aryl and/or may additionally be interrupted by an unsubstituted or substituted heteroatom.

The fused-on aryls of the radicals D are preferably benzene or naphthalene. Fused-on benzene rings are preferably unsubstituted or have 1, 2 or 3, in particular 1 or 2, substituents selected from among alkyl, alkoxy, halogen, SO$_3$H, sulfonate, NE$^1$E$^2$, alkylene-NE$^1$E$^2$, trifluoromethyl, nitro, carboxyl, alkoxycarbonyl and cyano. Fused-on naphthalenes are preferably unsubstituted or have, in the ring which is not fused on and/or in the fused-on ring, in each case 1, 2 or 3, in particular 1 or 2, of the substituents specified above for the fused-on benzene rings. Fused-on naphthalenes which are substituted in the fused-on ring preferably have a substituent in the ortho position relative to the phosphonite group. This is then preferably alkyl or alkoxycarbonyl. Alkyl as substituent of the fused-on aryls is preferably C$_1$–C$_4$-alkyl and in particular methyl, isopropyl or tert-butyl. Alkoxy is preferably C$_1$–C$_4$-alkoxy and in particular methoxy. Alkoxycarbonyl is preferably C$_1$–C$_4$-alkoxycarbonyl. Halogen is particularly preferably fluorine or chlorine.

If the C$_2$–C$_7$-alkylene bridge of the radical D is interrupted by 1, 2 or 3 unsubstituted or substituted heteroatoms, these are selected from among O, S and NR$^{18}$, where R$^{18}$ is alkyl, cycloalkyl or aryl. The C$_2$–C$_7$-alkylene bridge of the radical D is preferably interrupted by an unsubstituted or substituted heteroatom.

If the C$_2$–C$_7$-alkylene bridge of the radical D is substituted, it has 1, 2 or 3 substituents, in particular 1 substituent, which is/are selected from among alkyl, cycloalkyl and aryl, where the aryl substituent may bear 1, 2 or 3 of the substituents specified for aryl. The alkylene bridge D preferably has a substituent selected from among methyl, ethyl, isopropyl, phenyl, p-(C$_1$–C$_4$-alkyl)phenyl, preferably p-methylphenyl, p-(C$_1$–C$_4$-alkoxy)phenyl, preferably p-methoxyphenyl, p-halophenyl, preferably p-chlorophenyl, and p-trifluoromethylphenyl.

The radical D is preferably a C$_4$–C$_7$-alkylene bridge which is, as described above, fused and/or substituted and/or interrupted by unsubstituted or substituted heteroatoms. In particular, the radical D is a C$_4$–C$_5$-alkylene bridge which is fused with one or two phenyl and/or naphthyl groups, where the phenyl or naphthyl groups may bear 1, 2 or 3, in particular 1 or 2, of the abovementioned substituents.

The radical D (i.e. R$^6$ and R$^7$ together) together with the phosphorus atom and, if present, the oxygen atom(s) to which it is bound preferably forms a 5- to 8-membered heterocycle, where D (R$^6$ and R$^7$ together) is a radical selected from among the radicals of the formulae II.5 to II.9,

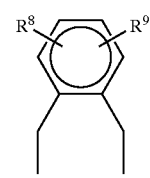
(II.5)

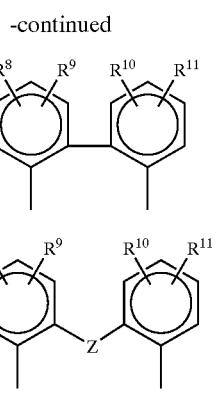
(II.6)

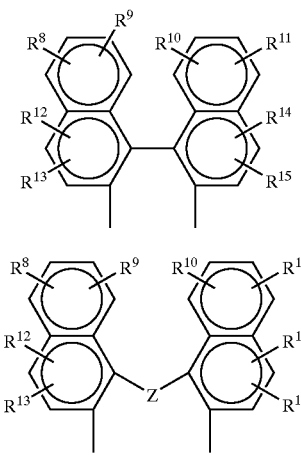
(II.7)

(II.8)

(II.9)

where
Z is O, S or NR$^{16}$, where
R$^{16}$ is alkyl, cycloalkyl or aryl,
or Z is a C$_1$–C$_3$-alkylene bridge which may contain a double bond and/or bear an alkyl, cycloalkyl or aryl substituent, where the aryl substituent may bear one, two or three substituents specified for aryl,
or Z is a C$_2$–C$_3$-alkylene bridge which is interrupted by O, S or NR$^{16}$,
R$^8$, R$^9$, R$^{10}$, R$^{11}$, R$^{12}$, R$^{13}$, R$^{14}$ and R$^{15}$ are each, independently of one another, hydrogen, alkyl, cycloalkyl, aryl, alkoxy, halogen, SO$_3$H, sulfonate, NE$^1$E$^2$, alkylene-NE$^1$E$^2$, trifluoromethyl, nitro, alkoxycarbonyl, carboxyl or cyano.

D is preferably a radical of the formula II.5 in which R$^8$ and R$^9$ are each hydrogen.

D is preferably a radical of the formula II.6a

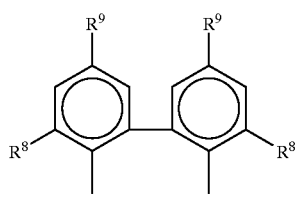
(II.6a)

where
R$^8$ is hydrogen, C$_1$–C$_4$-alkyl, SO$_3$H, sulfonate, NE$^1$E$^2$, alkylene-NE$^1$E$^2$, preferably hydrogen or C$_1$–C$_4$-alkyl, in particular methyl, isopropyl or tert-butyl,
R$^9$ is hydrogen, C$_1$–C$_4$-alkyl, preferably methyl, isopropyl or tert-butyl, C$_1$–C$_4$-alkoxy, preferably methoxy, fluorine, chlorine or trifluoromethyl. R$^9$ can also be SO$_3$H, sulfonate, NE$^1$E$^2$ or alkylene-NE$^1$E$^2$.

D is preferably a radical of the formula II.7a

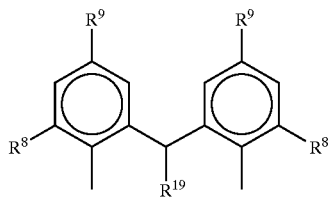
(II.7a)

where
R$^8$ and R$^9$ have the meanings given under the formula II.6a,
R$^{19}$ is hydrogen, C$_1$–C$_4$-alkyl, preferably methyl or ethyl, phenyl, p-(C$_1$–C$_4$-alkoxy)phenyl, preferably p-methoxyphenyl, p-fluorophenyl, p-chlorophenyl or p-(trifluoromethyl)phenyl.

D is preferably a radical of the formula II.8, in which R$^8$, R$^9$, R$^{10}$, R$^{11}$, R$^{12}$, R$^{13}$, R$^{14}$ and R$^{15}$ are each hydrogen.

D is preferably a radical of the formula II.8 in which R$^8$, R$^9$, R$^{10}$, R$^{11}$, R$^{13}$ and R$^{15}$ are each hydrogen and the radicals R$^{12}$ and R$^{14}$ are each, independently of one another, alkoxycarbonyl, preferably methoxycarbonyl, ethoxycarbonyl, n-propyloxycarbonyl or isopropyloxycarbonyl. In particular, the radicals R$^{12}$ and R$^{14}$ are located in the ortho position relative to the phosphorus atom or oxygen atom.

D is preferably a radical of the formula II.9 in which R$^8$, R$^9$, R$^{10}$, R$^{11}$, R$^{12}$, R$^{13}$, R$^{14}$ and R$^{15}$ are each hydrogen and Z is CR$^{19}$, where R$^{19}$ is as defined above.

D is preferably a radical of the formula II.9 in which R$^8$, R$^9$, R$^{10}$, R$^{11}$, R$^{13}$ and R$^{15}$ are each hydrogen, Z is CR$^{19}$ and the radicals R$^{12}$ and R$^{14}$ are each, independently of one another, alkoxycarbonyl, preferably methoxycarbonyl, ethoxycarbonyl, n-propyloxycarbonyl or isopropyloxycarbonyl. In particular, the radicals R$^{12}$ and R$^{14}$ are located in the ortho position relative to the phosphorus atom or oxygen atom.

In particular, the phosphorus-containing compound is selected from among compounds of the formulae I.i to I.v.

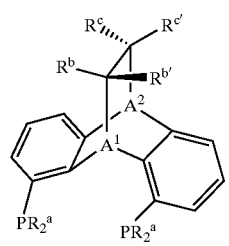
(I.i)

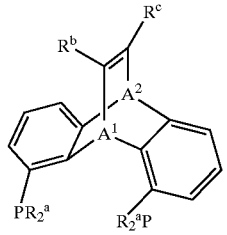
(I.ii)

-continued (I.iii)

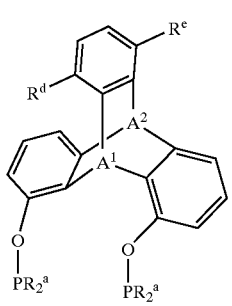

(I.iv)

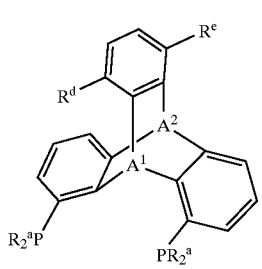

(I.v)

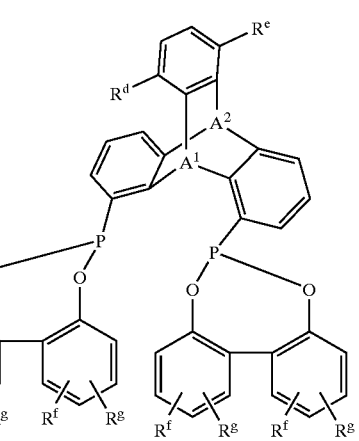

where $R^a$ is selected from among $C_1$–$C_6$-alkyl, $C_1$–$C_6$-alkoxy, $C_5$–$C_7$-cycloalkoxy, phenyl, phenoxy and pentafluorophenyl, where the phenyl- and phenoxy radicals may bear a substituent selected from among carboxyl, carboxylate, —$SO_3H$ and sulfonate, $R^b$, $R^{b'}$, $R^c$ and $R^{c'}$ are selected independently from among hydrogen, $C_1$–$C_6$-alkyl, $C_1$–$C_6$-alkoxy, $C_1$–$C_6$-alkoxycarbonyl and aryl, $R^d$ and $R^e$ are selected independently from among hydrogen and $C_1$–$C_6$-alkyl, $R^f$ and $R^g$ are selected independently from among hydrogen, $C_1$–$C_6$-alkyl and $C_1$–$C_6$-alkoxy, and $A^1$ and $A^2$ are each, independently of one another, N or $CR^5$, where $R^5$ is hydrogen or $C_1$–$C_8$-alkyl.

The radicals $R^b$, $R^{b'}$, $R^c$ and $R^{c'}$ are preferably selected from among hydrogen, methyl, ethyl, n-propyl, isopropyl, n-butyl, tert-butyl, methoxy, ethoxy, n-propoxy, isopropoxy, n-butoxy, tert-butoxy, methoxycarbonyl, ethoxycarbonyl and phenyl.

Examples of phosphorous-containing compounds preferred according to the present invention are shown below.

(I.1a-g)

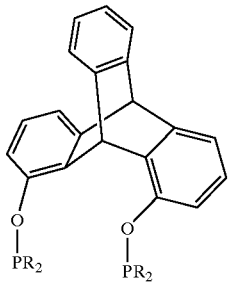

a: R = phenyl
b: R = cyclohexyl
c: R = isopropyl
d: R = tert-Butyl
e: R = phenoxy
f: R = ethoxy
g: R = $C_6F_5$
h: R = 3-$C_6H_4$—$SO_3Na$ (I.2a-h)

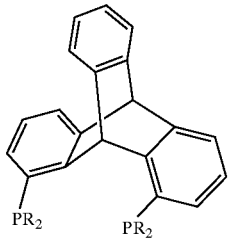

(I.3a-h)

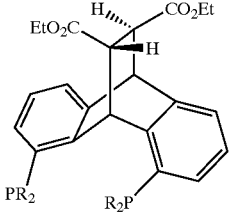

(I.4a-h)

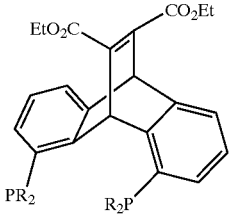

(I.5a-h)

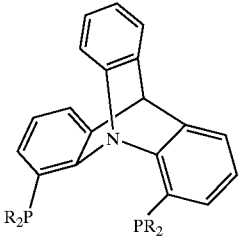

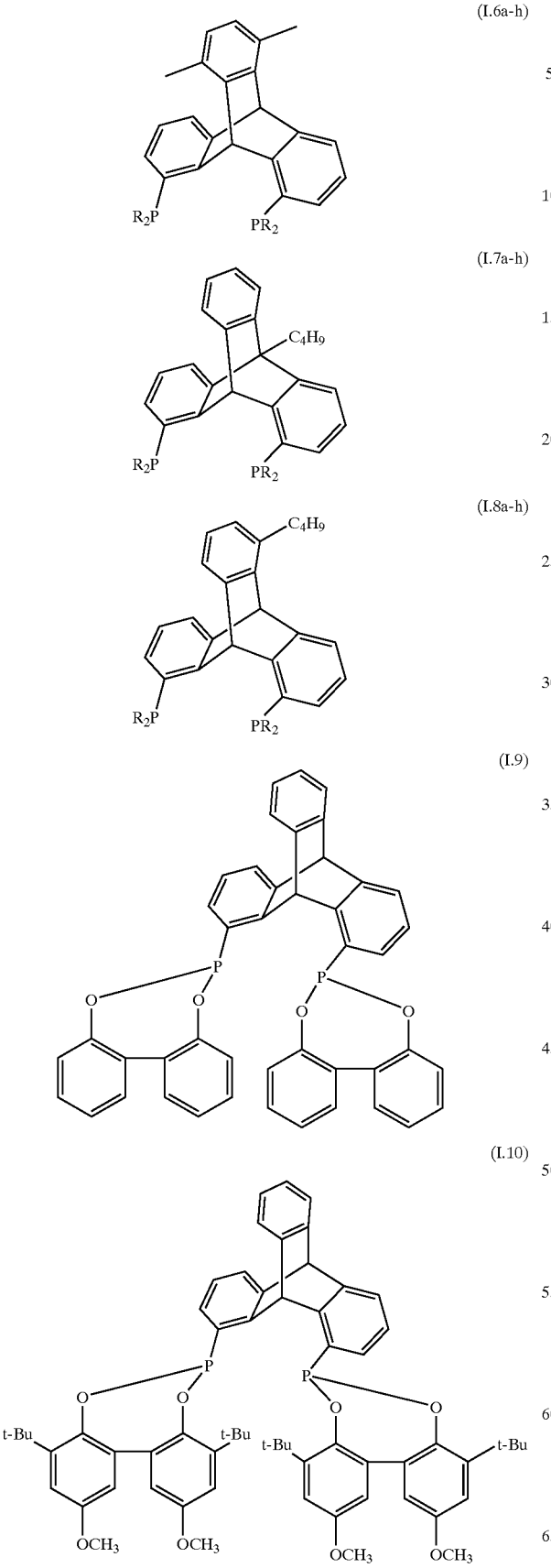

(I.6a-h)

(I.7a-h)

(I.8a-h)

(I.9)

(I.10)

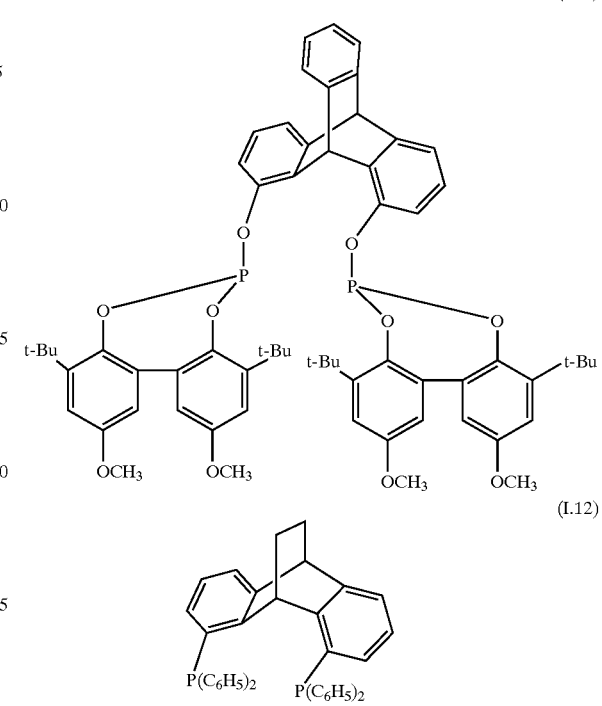

(I.11)

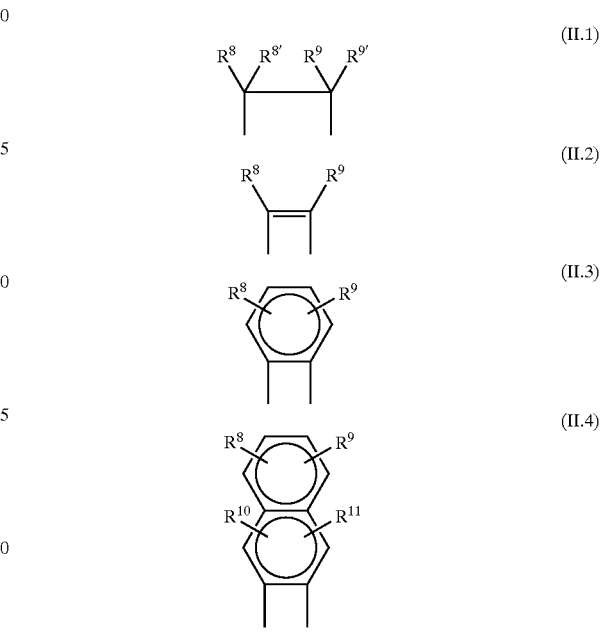

(I.12)

The compounds of the present invention are generally prepared by [4+2]-cycloaddition reactions, in the case of the compounds I based on bicyclo[2.2.2] parent structures preferably by [4+2]-cycloaddition (Diels-Alder reaction), of appropriately substituted anthracenes, acridines or analogous hetero compounds as diene components with dienophiles capable of forming the bridging groups X.

The present invention therefore also provides a process for preparing compounds of the formula I in which X is a radical of the formulae II.1, II.2, II.3 or II.4

(II.1)

(II.2)

(II.3)

(II.4)

where
$R^8$, $R^{8'}$, $R^9$, $R^{9'}$, $R^{10}$ and $R^{11}$ are each, independently of one another, hydrogen, alkyl, cycloalkyl, aryl, alkoxy, halogen, SO$_3$H, sulfonate, NE$^1$E$^2$, alkylene-NE$^1$E$^2$, trifluoromethyl, nitro, alkoxycarbonyl, carboxyl or cyano, by reacting a compound of the formula I.1

$$\text{(I.1)}$$

where

A$^1$ and A$^2$ are each, independently of one another, B, N, P or CR$^5$, where R$^5$ is hydrogen, alkyl, cycloalkyl, aryl, heteroaryl or a polymeric support which may be bound via a spacer group Y$^a$ and Y$^b$ are each, independently of one another, radicals Y$^1$ or Y$^2$ as defined above or Y$^a$ and Y$^b$ are each, independently of one another, halogen, OH, OC(O)CF$_3$ or SO$_3$Me where Me=hydrogen, Li, Na or K, where Y$^a$ and/or Y$^b$ can also be hydrogen if in each case one of the radicals R$^2$ and/or R$^4$ is an alkoxy group which is located in the ortho position of Y$^a$ and/or Y$^b$, R$^1$, R$^2$, R$^3$ and R$^4$ are each, independently of one another, hydrogen, alkyl, cycloalkyl, aryl, alkoxy, halogen, trifluoromethyl, nitro, alkoxycarbonyl or cyano, with a compound selected from among compounds of the formulae II.a, II.b, II.c or II.d $$R^8 \!-\! C \!\equiv\! C \!-\! R^9 \qquad \text{(II.a)}$$

$$R^8R^{8'}C \!=\! CR^9R^{9'} \qquad \text{(II.b)}$$

(II.c)

(II.d)

or a precursor of a compound of the formula II.c or II.d in a [4+2]-cycloaddition (Diels-Alder reaction) and, if desired, functionalizing radicals Y$^a$ and/or Y$^b$ to form radicals Y$^1$ and/or Y$^2$.

To prepare the compounds of the formula I.1, in which R$^1$, R$^2$, R$^3$ and R$^4$ are as defined above, which are used according to the present invention, it is possible, for example, to reduce a 1,8-dihalogen-substituted anthraquinone of the formula III, in which Y$^a$ and Y$^b$ have one of the above meanings and are, for example, halogen, in particular chlorine or bromine, according to scheme 1 below (III)

(I.1)

to give a compound of the formula I.1. Such reductions can be performed, for example, by means of zinc and ammonia and subsequent reaction with HCl/isopropanol, as is described, for example, in J. Org. Chem. 1980, 45, 1807–1817; J. Org. Chem. 1973, 38, 1167–1173; Bull. Chem. Soc. Jpn. 1971, 44, 1649–1652 and J. Am. Chem. Soc. 1969, 34, 3089–3092. Compound III can also be converted into compound I.1 by, for example, reaction of III with sodium borohydride and water (see T. R. Criswell et al., J. Org. Chem. 39 (1974), 770–774) or by reaction with aluminum alkoxides of cyclic alcohols, e.g. cyclohexanol, in the presence of these alcohols (see M. W. Haenel et al., Chem. Ber. 124, 1991, 333, and Fieser, Williamson, Organic Experiments, 3rd ed., 1975, p. 416ff. A suitable method of preparing 1,8-dichloroanthracene is disclosed in H. House, J. Org. Chem. 1986, 51, 921–929. The disclosure of these references is hereby fully incorporated by reference.

Examples of suitable compounds of the formula III are compounds of the formula III in which R$^1$, R$^2$, R$^3$ and R$^4$=hydrogen, and in which Ya and Yb are selected from among fluorine, chlorine, bromine, iodine, SO$_3$H, SO$_3$K, SO$_3$Na, OH, alkoxy such as methoxy or ethoxy. If two radicals R$^2$ and R$^4$ or R$^1$ and R$^3$ are each an alkoxy group located in the ortho position relative to Y$^a$ or Y$^b$, then Y$^a$ and Y$^b$ in III can also be hydrogen.

To build up the basic bicyclo[2.2.2] framework, the compound of the formula I.1 can, as described above, be reacted with a suitable dienophile, preferably selected from among compounds of the formulae II.a, II.b, II.c and II.d, according to scheme 2 below.

(I.1) $\xrightarrow[\text{[4+2]}]{\text{II.a – II.d}}$

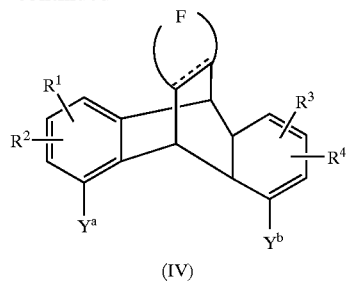

(IV)

In the formula IV, F is a radical derived from a compound II.a to II.d after removal of an etheno or ethyno group. If an acetylene derivative II.a is used for the Diels-Alder reaction, compounds IV which have an etheno bridge (shown by the dotted double bond) are formed.

Suitable compounds of the formula II.a are, for example, acetylenedicarboxylic acid and its monoesters and diesters with $C_1$–$C_8$-monoalcohols.

Suitable compounds of the formula II.b are, for example, maleic acid, fumaric acid and their monoesters and diesters with $C_1$–$C_8$-monoalcohols.

The dehydroaromatics II.c and II.d are preferably prepared in situ from suitable precursors and used for the [4.2]-cycloaddition. Suitable starting materials and methods are described, for example, in Carey, Sundberg, Advanced Organic Chemistry, $2^{nd}$ edition, part B, p. 402ff, Plenum Press, New York (1983), which is hereby incorporated by reference. The dehydroaromatics II.c and II.d are preferably prepared by diazotization of the corresponding ortho-aminocarboxylic acids according to scheme 3 below.

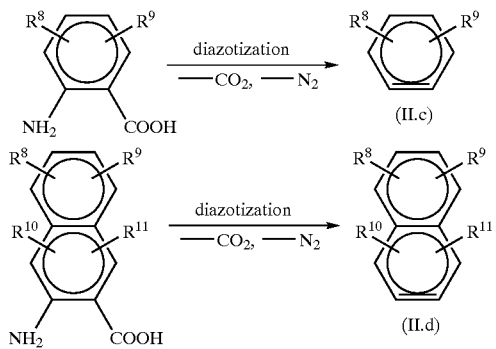

The diazotization is preferably carried out using alkyl nitrites such as n-butyl nitrite.

A suitable method of preparing 1,8-disubstituted ethanoanthracenes, e.g. 1,8-dichloroethanoanthracene, is described in JACS 94 (1972), pp. 3080–3088, which is hereby incorporated by reference.

The functionalization of the radicals $Y^a$ and $Y^b$ to form the radicals $Y^1$ and $Y^2$ can be carried out analogously to known methods. For example, compounds of the formula IV in which $Y^a$ and $Y^b$ are halogen, preferably chlorine, can firstly be lithiated and the intermediate formed can be reacted with a compound bearing a halogen atom, preferably a chlorine atom, on the phosphorus atom, for example a compound of the formula Cl—P($R^6$)$_2$, Cl—P($R_6$)($R_7$) or Cl—P($R^7$)$_2$. The compounds I which are particularly preferred according to the present invention, in which R is a radical of the formula III with z=0, are prepared, for example by reacting IV with compounds of the formula V according to scheme 4 below,

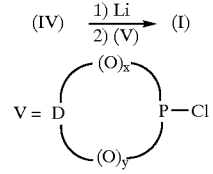

where x, y and D are as defined above for the compounds of the formula III.

In place of compounds of the formula IV in which $Y^a$=$Y^b$=halogen, it is also possible to lithiate compounds IV in which $Y^a$=$Y^b$=hydrogen and an alkoxy group or alkoxycarbonyl group is located in each of the ortho positions relative to $Y^a$ and $Y^b$. Such reactions are referred to as "ortho lithiation" in the literature (cf., for example, D. W. Slocum, J. Org. Chem., 1976, 41, 3652–3654; J. M. Mallan, R. L. Bebb, Chem. Rev., 1969, 693ff; V. Snieckus, Chem. Rev., 1980, 6, 879–933). The organolithium compounds obtained in this way can then be reacted with the phosphorus-halogen compounds in the abovementioned manner to give the target compounds I.

The preparation of the arsenic compounds and the antimony compounds I can be carried out analogously.

Compounds of the formula IV in which $Y^a$=$Y^b$=OH can be converted by sequential reaction with trifluoromethanesulfonic anhydride in the presence of a nitrogen base such as triethylamine and subsequently with a phosphide of the formula MeP($R^6$)$_2$, where Me is Li, Na or K, into compounds of the formula I in which $Y^a$=$Y^b$=P($R^6$)$_2$. Here, $R^6$ is selected from among those radicals mentioned above which are inert toward bases. MeP($R^6$)$_2$ is then, for example, KP($C_6H_5$)$_2$. This reaction can be carried out in a manner analogous to the reaction described by J. V. Allen et al. in Tetrahedron 50, 1994, p. 799–808.

Compounds IV in which $Y^a$=$Y^b$=$SO_3K$ or =$SO_3Na$ can be converted by reaction with a phosphide of the formula MeP($R^6$)$_2$, where $R^6$ is selected from among those radicals mentioned above which are inert toward bases, and Me is Li, Na or K, for example with KP($C_6H_5$)$_2$, into compounds of the formula I in which $Y^a$=$Y^b$=P($R^6$)$_2$. This reaction can be carried out in a manner analogous to the reactions described by M. W. Haenel, Chem. Ber. 124, 1991, p.333, or by H. Zorn, Chem. Ber. 98, 1965, p. 2431.

Compounds of the formula IV in which $Y^a$=$Y^b$=F can be converted into the corresponding diarylphosphines using a method analogous to the reaction described by Haenel in Synlett, 1988, 301–302.

The present invention further provides a catalyst comprising at least one complex of a metal of transition group VIII with at least one P-, As- or Sb-containing ligand selected from among compounds of the formula I, as described above.

The metal of transition group VIII is preferably selected from among cobalt, ruthenium, iridium, rhodium, nickel, palladium and platinum.

The catalysts of the present invention can comprise one or more of the phosphorus-containing compounds of the formula I. In addition to the above-described ligands of the formula I, they can also have at least one further ligand selected from among halides, amines, carboxylates, acetylacetonate, arylsulfonates and alkylsulfonates, hydride, CO, olefins, dienes, cycloolefins, nitrites, N-containing heterocycles, aromatics and heteroaromatics, ethers, $PF_3$, phospholes, phosphabenzenes and monodentate, bidentate and polydentate phosphine, phosphinite, phosphonite, phosphoramidite and phosphite ligands.

An object of the present invention is also to make available an improved process for the hydroformylation of compounds containing at least one ethylenically unsaturated double bond. Here, a very high proportion of α-aldehydes or α-alcohols should preferably be achieved in the hydroformylation of α-olefins. In particular, the process should be suitable for the hydroformylation of internal linear olefins with a high regioselectivity in respect of terminal product aldehydes.

The invention also provides a process for the hydroformylation of compounds containing at least one ethylenically unsaturated double bond by reaction with carbon monoxide and hydrogen in the presence of at least one hydroformylation catalyst selected from among the above-described catalysts of the present invention.

In general, the catalysts or catalyst precursors used in each case are converted under hydroformylation conditions into catalytically active species of the formula $H_xM_y(CO)_zL_q$, where M is a metal of transition group VIII, L is a phosphorus-containing compound according to the present invention and q, x, y, z are integers which depend on the valence and type of the metal and on the number of coordination positions occupied by the ligand L. z and q are preferably, independently of one another, each at least 1, e.g. 1, 2 or 3. The sum of z and q is preferably from 2 to 5. If desired, the complexes can additionally contain at least one of the further ligands described above.

The metal M is preferably cobalt, ruthenium, rhodium, nickel, palladium, platinum, osmium or iridium and particularly preferably cobalt, ruthenium, iridium, rhodium, nickel, palladium or platinum.

In a preferred embodiment, the hydroformylation catalysts are prepared in situ in the reactor used for the hydroformylation reaction. However, the catalysts of the present invention can also, if desired, be prepared separately and isolated by customary methods. For in-situ preparation of the catalysts of the present invention, it is possible, for example, to react at least one phosphorus-containing compound of the formula I, a compound or a complex of a metal of transition group VIII, if desired at least one further additional ligand and, if desired, an activating agent in an inert solvent under the hydroformylation conditions.

Suitable rhodium compounds or complexes are, for example, rhodium(II) and rhodium(III) salts, e.g. rhodium (III) chloride, rhodium(III) nitrate, rhodium(III) sulfate, potassium rhodium sulfate, rhodium(II) or rhodium(III) carboxylates, rhodium(II) and rhodium(III) acetate, rhodium (III) oxide, salts of rhodic(III) acid, trisammonium hexachlororhodate(III), etc. Also suitable are rhodium complexes such as dicarbonylrhodium acetylacetonate, acetylacetonatobisethylenerhodium(I), etc. Preference is given to using dicarbonylrhodium acetylacetonate or rhodium acetate.

Likewise suitable are ruthenium salts or compounds. Suitable ruthenium salts are, for example, ruthenium(III) chloride, ruthenium(IV), ruthenium(VI) or ruthenium(VIII) oxide, alkali metal salts of oxo acids of ruthenium, e.g. $K_2RuO_4$ or $KRuO_4$, or complexes such as $RuHCl(CO)(PPh_3)_3$. It is also possible to use metal carbonyls of ruthenium, e.g. dodecacarbonyltriruthenium or octadecacarbonylhexaruthenium, or mixed forms in which CO is partly replaced by ligands of the formula $PR_3$, e.g. $Ru(CO)_3(PPh_3)_2$, in the process of the present invention.

Suitable cobalt compounds are, for example, cobalt(II) chloride, cobalt(II) sulfate, cobalt(II) carbonate, cobalt(II) nitrate, their amine or hydrate complexes, cobalt carboxylates such as cobalt acetate, cobalt ethylhexanoate, cobalt naphthanoate, and also the cobalt caprolactamate complex. Here too, the carbonyl complexes of cobalt, e.g. octacarbonyldicobalt, dodecacarbonyltetracobalt and hexadecacarbonylhexacobalt, can be used.

The abovementioned and further suitable compounds of cobalt, rhodium, ruthenium and iridium are known in principle and are adequately described in the literature or can be prepared by a person skilled in the art using methods analogous to those for the known compounds.

Suitable activating agents are, for example, Brönsted acids, Lewis acids such as $BF_3$, $AlCl_3$, $ZnCl_2$, and Lewis bases.

As solvents, preference is given to using the aldehydes formed in the hydroformylation of the respective olefins, and also their higher-boiling subsequent reaction products, e.g. the products of aldol condensation. Other suitable solvents are aromatics such as toluene and xylenes, hydrocarbons or mixtures of hydrocarbons, also for dilution of the abovementioned aldehydes and subsequent products of the aldehydes. Further solvents are esters of aliphatic carboxylic acids with alkanols, for example ethyl acetate or Texanol™, ethers such as tert-butyl methyl ether and tetrahydrofuran. In the case of sufficiently hydrophilic ligands, it is also possible to use alcohols, such as methanol, ethanol, n-propanol, isopropanol, n-butanol and isobutanol, and ketones such as acetone and methyl ethyl ketone, etc. Furthermore, "ionic liquids" can also be used as solvents. These are liquid salts, for example N,N'-dialkylimidazolium salts such as N-butyl-N'-methylimidazolium salts, tetraalkylammonium salts such as tetra-n-butylammonium salts, N-alkylpyridinium salts such as n-butylpyridinium salts, tetraalkylphosphonium salts such as trishexyl(tetradecyl)phosphonium salts, e.g. the tetrafluoroborates, acetates, tetrachloroaluminates, hexafluorophosphates, chlorides and tosylates.

Furthermore, it is also possible to carry out the reactions in water or aqueous solvent systems comprising water together with a water-miscible solvent, for example an alcohol such as methanol, ethanol, n-propanol, isopropanol, n-butanol or isobutanol, a ketone such as acetone or methyl ethyl ketone or another solvent. For this purpose, use is made of ligands of the formula I which are modified with polar groups, for example ionic groups such as $SO_3Me$, $CO_2Me$ where Me=Na, K or $NH_4$ or $N(CH_3)_3^+$. The reactions then proceed in a two-phase catalyzed system in which the catalyst is present in the aqueous phase and starting materials and products form the organic phase. The reaction in the "ionic liquids" can also be carried out as a two-phase catalyzed system.

The molar ratio of the phosphorus-containing ligand to the metal of transition group VIII is generally in a range from about 1:1 to 1 000:1.

Suitable substrates for the hydroformylation process of the present invention are in principle all compounds which contain one or more ethylenically unsaturated double bonds. These include, for example, olefins such as α-olefins, internal straight-chain and internal branched olefins. Suitable α-olefins are, for example, ethylene, propene, 1-butene, 1-pentene, 1-hexene, 1-heptene, 1-octene, 1-nonene, 1-decene, 1-undecene, 1-dodecene, etc.

Preferred straight-chain internal olefins are $C_4$–$C_{20}$-olefins such as 2-butene, 2-pentene, 2-hexene, 3-hexene, 2-heptene, 3-heptene, 2-octene, 3-octene, 4-octene, etc.

Preferred branched, internal olefins are $C_4$–$C_{20}$-olefins such as 2-methyl-2-butene, 2-methyl-2-pentene or 3-methyl-2-pentene, branched, internal heptene mixtures, branched, internal octene mixtures, branched, internal nonene mixtures, branched, internal decene mixtures, branched, internal undecene mixtures and branched, internal dodecene mixtures, etc.

Further olefins suitable for the hydroformylation process are $C_5$–$C_8$-cycloalkenes such as cyclopentene, cyclohexene, cycloheptene, cyclooctene and their derivatives, e.g. their $C_1$–$C_{20}$-alkyl derivatives having from 1 to 5 alkyl substituents. Vinylaromatics such as styrene, α-methylstyrene, 4-isobutylstyrene, etc., are also suitable olefins for the hydroformylation process. Further suitable olefins for hydroformylation are α,β-ethylenically unsaturated monocarboxylic and/or dicarboxylic acids, their esters, monoesters and amides, e.g. acrylic acid, methacrylic acid, maleic acid, fumaric acid, crotonic acid, itaconic acid, methyl 3-pentenoate, methyl 4-pentenoate, methyl oleate, methyl acrylate, methyl methacrylate, unsaturated nitriles such as 3-pentenenitrile, 4-pentenenitrile, acrylonitrile, vinyl ethers such as vinyl methyl ether, vinyl ethyl ether, vinyl propyl ether, etc., $C_1$–$C_{20}$-alkenols, -alkenediols and -alkadienols, e.g. 2,7-octadien-1-ol. A preferred alkenol is allyl alcohol. Further suitable substrates are dienes or polyenes having isolated or conjugated double bonds. These include, for example, 1,3-butadiene, 1,4-pentadiene, 1,5-hexadiene, 1,6-heptadiene, 1,7-octadiene, vinylcyclohexene, dicyclopentadiene, 1,5,9-cyclooctatriene and also homopolymers and copolymers of butadiene.

Preference is given to a process in which the hydroformylation catalyst is prepared in situ by reacting at least one P-, As- or Sb-containing compound according to the present invention, a compound or a complex of a metal of transition group VIII and, if desired, an activating agent in an inert solvent under the hydroformylation conditions.

The hydroformylation reaction can be carried out continuously, semicontinuously or batchwise.

Suitable reactors for a continuous reaction are known to those skilled in the art and are described, for example, in Ullmanns Enzyklopädie der technischen Chemie, vol. 1, $3^{rd}$ edition, 1951, p. 743 ff.

Suitable pressure reactors are likewise known to those skilled in the art and are described, for example, in Ullmanns Enzyklopädie der technischen Chemie, vol. 1, $3^{rd}$ edition, 1951, p. 769 ff. In general, the process of the present invention is carried out using an autoclave which may, if desired, be provided with a stirring device and internal lining.

The composition of the synthesis gas, viz. a mixture of carbon monoxide and hydrogen, used in the process of the present invention can vary within wide limits. The molar ratio of carbon monoxide to hydrogen is generally from about 5:95 to 70:30, preferably from about 40:60 to 60:40. Particular preference is given to using a molar ratio of carbon monoxide to hydrogen in the region of about 1:1.

The temperature in the hydroformylation reaction is generally in a range from about 20 to 180° C., preferably from about 50 to 150° C. The reaction is generally carried out at the partial pressure of the reaction gas at the chosen reaction tempereature. In general, the pressure is in a range from about 1 to 700 bar, preferably from 1 to 600 bar, in particular from 1 to 300 bar. The reaction pressure can be varied as a function of the activity of the hydroformylation catalyst of the present invention used. In general, the catalysts of the present invention based on phosphorus-containing compounds allow reaction at relatively low pressures, for example from 1 to 100 bar.

The hydroformylation catalysts of the present invention can be separated from the output from the hydroformylation reaction by customary methods known to those skilled in the art and can generally be reused for the hydroformylation.

Advantageously, the catalysts of the present invention display a high activity, so that the corresponding aldehydes are generally obtained in good yields. In addition, in the hydroformylation of α-olefins and of internal, linear olefins, they display a very low selectivity to the hydrogenation product of the olefin used. Surprisingly, the hydroformylation activity of catalysts based on compounds of the formula I is generally higher than the isomerization activity in respect of the formation of internal double bonds. In the hydroformylation of α-olefins, the catalysts of the present invention advantageously display a high selectivity to the α-aldehydes or α-alcohols. In addition, good yields of α-aldehdyes or α-alcohols and particularly also n-aldehydes or n-alcohols are generally also obtained in the hydroformylation of internal linear olefins (isomerizing hydroformylation).

The above-described, novel catalysts which comprise chiral compounds of the formula I are suitable for enantioselective hydroformylation.

The invention further provides for the use of catalysts comprising one of the above-described P-, As- or Sb-containing compounds for the hydroformylation of compounds having at least one ethylenically unsaturated double bond.

A further field of use for the catalysts of the present invention is the hydrocyanation of olefins. The hydrocyanation catalysts of the present invention also comprise complexes of a metal of transitition group VIII, in particular cobalt, nickel, ruthenium, rhodium, palladium, platinum, preferably nickel, palladium and platinum and very particularly preferably nickel. The metal is generally present in the metal complex of the present invention in zero-valent form. The preparation of the metal complexes can be carried out as described above for use as hydroformylation catalysts. The same applies to the in-situ preparation of the hydrocyanation catalysts of the present invention.

An example of a nickel complex suitable for preparation of a hydrocyanation catalyst is bis(1,5-cyclooctadiene) nickel(0).

If desired, the hydrocyanation catalysts can be prepared in situ in a manner analogous to the methods described for the hydroformylation catalysts.

The present invention therefore also provides a process for preparing nitriles by catalytic hydrocyanation, in which the hydrocyanation is carried out in the presence of at least one of the above-described novel catalysts. Suitable olefins for hydrocyanation are generally the olefins mentioned above as starting materials for hydroformylation. A specific embodiment of the process of the present invention relates to the preparation of mixtures of monoolefinic $C_5$-mononitriles having nonconjugated C=C— and C≡N bonds by catalytic hydrocyanation of 1,3-butadiene or 1,3-butadiene-containing hydrocarbon mixtures and isomerization/further reaction to form saturated $C_4$-dinitriles, preferably adiponitrile, in the presence of at least one catalyst according to the present invention. When hydrocarbon mixtures are used for preparing monoolefinic $C_5$-mononitriles by the process of the present invention, preference is given to using a hydrocarbon mixture which has a 1,3-butadiene content of at least 10% by volume, preferably at least 25% by volume, in particular at least 40% by volume.

1,3-Butadiene-containing hydrocarbon mixtures are obtainable on an industrial scale. Thus, for example, the processing of petroleum by steam cracking of naphtha produces a hydrocarbon mixture known as $C_4$ fraction which has a high total olefin content of which about 40% is made up by 1,3-butadiene and the remainder is made up of monoolefins and multiply unsaturated hydrocarbons and also alkanes. These streams always additionally contain small proportions of generally up to 5% of alkynes, 1,2-dienes and vinylacetylene.

Pure 1,3-butadiene can be isolated from industrially available hydrocarbon mixtures by, for example, extractive distillation.

The catalysts of the present invention can advantageously be used for the hydrocyanation of such olefin-containing, in particular 1,3-butadiene-containing, hydrocarbon mixtures, generally even without prior purification of the hydrocarbon mixture by distillation. Olefins which may possibly be present and reduce the effectiveness of the catalysts, e.g. alkynes or cumulenes, may be removed from the hydrocarbon mixture by selective hydrogenation prior to the hydrocyanation. Suitable selective hydrogenation processes are known to those skilled in the art.

The hydrocyanation of the present invention can be carried out continuously, semicontinuously or batchwise. Suitable reactors for continuous reaction are known to those skilled in the art and are described, for example, in Ullmanns Enzyklopädie der technischen Chemie, volume 1, 3$^{rd}$ edition, 1951, p. 743 ff. The continuous variant of the process of the present invention is preferably carried out using a cascade of stirred vessels or a tube reactor. Suitable reactors, which may be pressure-rated, for the semicontinuous or continuous embodiment are known to those skilled in the art and are described, for example, in Ullmanns Enzyklopädie der technischen Chemie, volume 1, 3$^{rd}$ edition, 1951, p. 769 ff. In general, the process of the present invention is carried out using an autoclave which may, if desired, be provided with a stirring device and internal lining.

The hydrocyanation catalysts of the present invention can be separated from the output from the hydrocyanation reaction by customary methods known to those skilled in the art and can generally be reused for the hydrocyanation.

The present invention further provides a process for the carbonylation of compounds containing at least one ethylenically unsaturated double bond by reaction with carbon monoxide and at least one compound having a nucleophilic group in the presence of a carbonylation catalyst, wherein the carbonylation catalyst used is a catalyst based on a P-, As- or Sb-containing ligand of the formula I.

The carbonylation catalysts of the present invention also comprise complexes of a metal of transition group VIII, preferably nickel, cobalt, iron, ruthenium, rhodium and palladium, in particular palladium. The metal complexes can be prepared as described above in the case of the hydroformylation catalysts and hydrocyanation catalysts. The same applies to the in-situ preparation of the carbonylation catalysts of the present invention.

Suitable olefins for the carbonylation are the olefins mentioned above in general terms as starting materials for the hydroformylation and hydrocyanation.

The compounds having a nucleophilic group are preferably selected from among water, alcohols, thiols, carboxylic esters, primary and secondary amines.

A preferred carbonylation reaction is the conversion of olefins into carboxylic acids by reaction with carbon monoxide and water (hydrocarboxylation). This includes, in particular, the reaction of ethylene with carbon monoxide and water to give propionic acid.

The invention further provides for the use of catalysts comprising a P-, As- or Sb-containing compound according to the present invention, as described above, for hydroformylation, hydrocyanation, carbonylation, hydrogenation, oligomerization and polymerization of olefins and for metathesis.

The invention is illustrated by the following, nonlimiting examples.

EXAMPLES

I. Preparation of Compounds I

Example 1

1,8-Bis(diphenylphosphino)triptycene (=1,8-bis (diphenylphosphino)-9,10-dihydro-9,10-benzoanthracene) (Ligand A)

1.1 Preparation of 1,8-dichloroanthracene 25 g (91 mmol) of 1,8-dichloroanthraquinone and 65 g (1 mol) of Zn dust were suspended in 1 l of a 20% strength by weight aqueous ammonia solution and the mixture was refluxed for 3 hours. After cooling to room temperature, the solid was separated off via a Büchner funnel. The aqueous phase was extracted three times with 150 ml each time of dichloromethane; the solid was extracted a number of times with dichloromethane while being treated with ultrasound. The combined organic phases were dried over magnesium sulfate and freed of the solvent on a rotary evaporator. The solid, whitish yellow residue was suspended in 600 ml of propanol and 65 ml of 12M hydrochloric acid and the mixture was refluxed for three hours. The solvent was subsequently removed under reduced pressure, the residue was taken up in dichloromethane, the solution was washed with saturated sodium hydrogen carbonate solution and dried over magnesium sulfate. Removal of the solvent gave 1,8-dichloroanthracene as a yellow solid which was recrystallized from propanol.

Yield: 9.4 g (38 mmol)=42% of theory.

Melting point: 155° C. (literature: 156–158° C.).

1.2 Preparation of 1,8-dichlorotriptycene 6.97 g (28 mmol) of 1,8-dichloroanthracene were suspended in 120 ml of 1,2-dichloroethane and the mixture was heated to reflux. 3.2 g (31 mmol) of n-butyl nitrite were added to the yellow solution, and a solution of 4 g (29 mmol) of anthranilic acid in 25 ml of 2-ethoxyethyl ether was added dropwise to the resulting mixture. After half an hour, the solvent was distilled from the black solution until the temperature at the distillation head was 150° C. After addition of 2 g (20 mmol) of maleic anhydride, the mixture was refluxed for three minutes, subsequently cooled by means of an icebath and a solution of 67 ml of methanol, 34.4 ml of water and 8 g of potassium hydroxide was then added. The brown solid was filtered off and washed with methanol:water in a ratio of 4:1 until the washings were colorless. The flesh-colored solid was dissolved in 2-butanone, admixed with 200 mg of activated carbon and this mixture was refluxed for one hour. After filtering off the activated carbon, the clear solution was concentrated by evaporation and the product was allowed to crystallize in a refrigerator. Addition of methanol resulted in crystallization of further product. The product can be recrystallized from 2-butanone.

Yield: 5.61 mg (17 mmol)=62%.

Melting point: 297° C. (literature: 299.5–300° C.).

1.3 Preparation of 1,8-bis(diphenylphosphino)triptycene

All steps were carried out with exclusion of oxygen and water in a protective argon gas atmosphere.

A solution of 485 mg (1.5 mmol) of 9,10-benzo-1,8-dichloro-9,10-dihydroanthracene in 20 ml of tetrahydrofuran was added dropwise over the course of one hour to a suspension of 82 mg (12 mmol) of lithium powder in 10 ml of tetrahydrofuran which had been cooled to −78° C. The resulting red suspension was kept at −78° C. for a further seven hours, after which 772 mg (3.5 mmol) of diphenylchlorophosphine were added to the filtrate, cooling was removed and the yellow solution was stirred at room temperature for four hours. After removal of the solvent under reduced pressure, the remaining solid was admixed with water and extracted with dichloromethane. The solvent phase was dried over magnesium sulfate. After removal of the dichloromethane under reduced pressure, the product was recrystallized from toluene.

Yield: 392 mg (0.63 mmol)=42%.
Characterization:
$^{31}$P-NMR (CDCl$_3$, 121.495 MHz, 300K): δ=−14.7.
$^1$H-NMR (C$_6$D$_6$, 300.132 MHz, 300K): δ=5.20 (s, 1H, H10), 6.18 (s, 1H, H9), 6.62–7.34 (m, H—Ar).
$^{13}$C-NMR (CDCl$_3$, 75.469 MHz, 300K): δ=29.7 (C10), 59.0 (C9), 122.7–145.6 (C—Ar).

Example 2

1,8-Bis(diphenylphosphino)-9,10-ethanoanthracene (Ligand B)

2.1 The preparation of 1,8-dichloroanthracene was carried out as described in 1.1.
2.2 1,8-Dichloranthracene was reacted with ethene in a Diels-Alder reaction to a give 1,8-dichloro-9,10-dihydro-9,10-ethanoanthracene, using the method in JACS 94(9) (1972), pp. 3080–3088.
2.3 The preparation of 1,8-bis(diphenylphosphino)-9,10-dihydro-9,10-ethanoanthracene was carried out by lithiation and reaction with diphenylchlorophosphane, as described in 1.3.

II Examination of the Catalytic Action of Transition Metal Complexes with Ligands of the Formula I Example 3

1.6 mg of dicarbonylrhodium(II) 2,4-pentanedionate (Rh(CO)$_2$acac) and 19 mg of 1,8-bis(diphenylphosphino)triptycene (ligand A, ligand:metal ratio=5:1 mol/mol) were dissolved in 5 ml of toluene and subsequently heated at 100° C. for 30 minutes under a synthesis gas pressure of 10 bar (H$_2$/CO atmosphere having a molar ratio of 1:1) in an autoclave. 5 g of 1-octene were then added, a synthesis gas pressure of 5 bar was set and the temperature was held for 4 hours. The reaction product was analyzed by gas chromatography. The conversion based on 1-octene used was 43%. The selectivity to the formation of nonanal was 92%. The proportion of n-nonanal was 99.2%.

Example 4

1.6 mg of dicarbonylrhodium acetylacetonate and 57 mg of ligand A (ligand-metal ratio=15:1) were dissolved in 5 g of toluene and subsequently heated at 100° C. for 30 minutes under a CO/H$_2$ (1:1) pressure of 10 bar in a glass autoclave. 5 g of 1-octene were subsequently added and a synthesis gas pressure of 10 bar was set for 4 hours. Analysis of the reaction product showed a conversion of 1-octene of 77% with an aldehyde selectivity of 98% and a linearity of 99%. The proportion of α-aldehyde was 100%.

Example 5

1.6 mg of dicarbonylrhodium acetylacetonate, 76 mg of ligand A and 16 mg of triphenylphosphine (triptyphos:triphenylphosphine:rhodium ratio=20:10:1) were dissolved in 5 g of toluene and subsequently heated at 100° C. for 30 minutes under a CO/H$_2$ (1:1) pressure of 10 bar in a glass autoclave. 5 g of 1-octene were subsequently added, the mixture was heated to 120° C. and a synthesis gas pressure of 10 bar was set for 4 hours. Analysis of the reaction product showed a conversion of 1-octene of 97% with an aldehyde selectivity of 92% and a linearity of 99%. The proportion of α-aldehyde was 100%.

Example 6

5.42 mg of dicarbonylrhodium acetylacetonate and 181.3 mg of ligand B were separately dissolved in 5.5 g each of diphenyl ether, combined and preactivated at 100° C. for 30 minutes under a synthesis gas pressure (CO:H$_2$=1:1) of 10 bar. 11 g of 1-octene (purity: 97% of 1-octen; remainder: internal octenes) were subsequently added by means of a lock, and the mixture was hydroformylated at 100° C. and 10 bar for 4 hours. Analysis of the reaction product by means of gas chromatography indicated a conversion of 1-octene of 98%. The aldehyde selectivity was 96%, the proportion of n-aldehyde was 99% and the proprotion of α-aldehyde (n-aldehyde and iso-aldehyde) was 100%.

It can be seen from this that use of the novel catalysts enables terminal olefins to be converted into terminal aldehydes with high linearity and very good activity and at the same time with minimal isomerization to internal olefins.

What is claimed is:
1. A compound of formula I

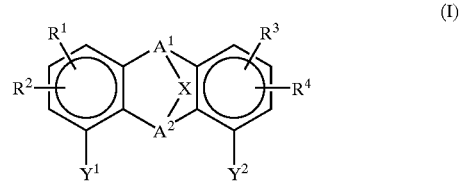

where
A$^1$ and A$^2$ are each, independently of one another, B, N, P or CR$^5$, where R$^5$ is hydrogen, alkyl, cycloalkyl, aryl or heteroaryl, or R$^5$ is a polymeric support which is optionally bound via a spacer group, X is O, S, NR$^a$, where R$^a$ is hydrogen, alkyl, cycloalkyl or aryl, or is a C$_1$–C$_{10}$-alkylene bridge which optionally meets one or more of the following requirements (a) to (d):

(a) the bridge has one, two, three or four double bonds,
(b) the bridge carries one, two, three or four substituents selected from a group consisting of:
alkyl, alkoxy, halogen, nitro, cyano, carboxyl, carboxylate, cycloalkyl and aryl, where the aryl substituent is optionally substituted by one, two or three substituents selected from a group consisting of alkyl, alkoxy, halogen, SO$_3$H, sulfonate, NE$^1$E$^2$, alkylene-NE$^1$E$^2$, trifluoromethyl, nitro, alkoxycarbonyl and cyano,
(c) the bridge is interrupted by one, two or three nonadjacent, substituted or unsubstituted heteroatoms,
(d) the bridge is fused with one, two or three rings selected from a group consisting of aryl and heteroaryl rings, where the fused-on rings optionally carry one, two or three substituents selected from a group consisting of:
alkyl, cycloalkyl, aryl, alkoxy, cycloalkoxy, aryloxy, acyl, halogen, SO$_3$H, sulfonate, trifluoromethyl, nitro, cyano, carboxyl, alkoxycarbonyl, NE$^1$E$^2$ and alkylene-NE$^1$E$^2$, Y¹ and Y² each represents, independently of one another, a group containing one atom selected from the group consisting of phosphorus, arsenic and antimony, which atom is bound directly or via an oxygen atom to the phenyl ring in formula I, $R^1$, $R^2$, $R^3$ and $R^4$ are each, independently of one another, hydrogen, alkyl, cycloalkyl, aryl, alkoxy, halogen, $NE^1E^2$, alkylene-$NE^1E^2$, trifluoromethyl, nitro, alkoxycarbonyl or cyano, and $E^1$ and $E^2$ are identical or different and each represents alkyl, cycloalkyl or aryl.

2. A compound of the formula I as defined in claim 1 in which at least one of $A^1$ and $A^2$ is $CR^5$, where $R^5$ is a polymeric support which is optionally bound via a spacer group.

3. A compound as claimed in claim 1, wherein $Y^1$ and $Y^2$ each represent, independently of one another, a group of formula $PR^6R^7$, $P(OR^6)R^7$, $P(OR^6)(OR^7)$, $OPR^6R^7$, $OP(OR^6)R^7$ or $OP(OR^6)(OR^7)$, where $R^6$ and $R^7$ are each, independently of one another, alkyl, cycloalkyl, aryl or heteroaryl which optionally carry one, two or three substituents selected from a group consisting of:
  alkyl, cycloalkyl, aryl, alkoxy, cycloalkyloxy, aryloxy, halogen, trifluoromethyl, nitro, cyano, carboxyl, carboxylate, acyl, $SO_3H$, sulfonate, $NE^1E^2$ and alkylene-$NE^1E^2$, or $R^6$ and $R^7$ together with the phosphorus atom and, where present, the oxygen atom(s) to which they are bound form a 5- to 8-membered heterocycle, wherein the heterocycle is optionally fused with one, two or three ring selected from a group consisting of cycloalkyl, aryl and heteroaryl rings, and the fused-on rings are, independently of one another, optionally substituted by one, two, three or four substituents selected from a group consisting of:
  alkyl, alkoxy, halogen, $SO_3H$, sulfonate, $NE^1E^2$, alkylene-$NE^1E^2$, nitro, cyano, carboxyl and carboxylate, and where the heterocycle optionally contains one or two additional heteroatoms selected from a group consisting of N, O and S.

4. A compound as claimed in claim 1, wherein X is a $C_1$–$C_{10}$-alkylene bridge which optionally meets one or more of the following requirements (a) to (d):
  (a) the bridge has one, two, three or four double bonds,
  (b) the bridge carries one, two, three or four substituents selected from a group consisting of:
    alkyl, alkoxy, halogen, nitro, cyano, carboxyl, carboxylate, cycloalkyl and aryl, where the aryl substituent is optionally substituted by one, two or three substituents selected from a group consisting of alkyl, alkoxy, halogen, $SO_3H$, sulfonate, $NE^1E^2$, alkylene-$NE^1E^2$, trifluoromethyl, nitro, alkoxycarbonyl and cyano,
  (c) the bridge is interrupted by one, two or three nonadjacent, substituted or unsubstituted heteroatoms,
  (d) the bridge is fused with one, two or three rings selected from aryl and heteroaryl rings, where the fused-on rings optionally carry one, two or three substituents selected from a group consisting of:
    alkyl, cycloalkyl, aryl, alkoxy, cycloalkoxy, aryloxy, acyl, halogen, $SO_3H$, sulfonate, trifluoromethyl, nitro, cyano, carboxyl, alkoxycarbonyl, $NE^1E^2$ and alkylene-$NE^1E^2$.

5. A compound as claimed in claim 4, wherein X is a moiety of formulae II.1 to II.10

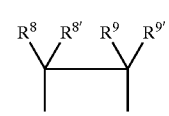 (II.1)

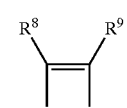 (II.2)

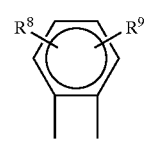 (II.3)

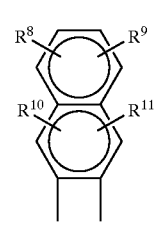 (II.4)

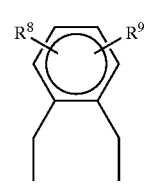 (II.5)

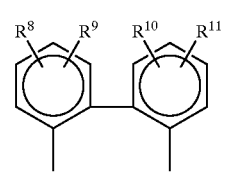 (II.6)

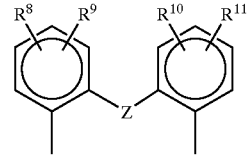 (II.7)

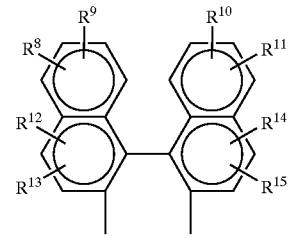 (II.8)

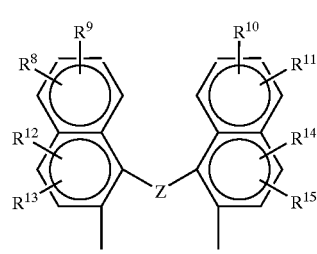 (II.9)

-continued (II.10)

where

Z is O, S or NR$^{16}$, where R$^{16}$ is alkyl, cycloalkyl or aryl, or

Z is a C$_1$–C$_3$-alkylene bridge which optionally meets one or both of the following requirements (a) and (b):
(a) the bridge has a double bond,
(b) the bridge carries an alkyl, cycloalkyl or aryl substituent, where the aryl substituent is optionally substituted by one, two or three substituents selected from a group consisting of alkyl, alkoxy, halogen, SO$_3$H, sulfonate, NE$^1$E$^2$, alkylene-NE$^1$E$^2$, trifluoromethyl, nitro, alkoxycarbonyl and cyano, or Z is a C$_2$–C$_3$-alkylene bridge which is interrupted by O, S or NR$^{16}$, R$^8$, R$^{8'}$, R$^9$, R$^{9'}$, R$^{10}$, R$^{11}$, R$^{12}$, R$^{13}$, R$^{14}$ and R$^{15}$ are each, independently of one another, hydrogen, alkyl, cycloalkyl, aryl, alkoxy, halogen, SO$_3$H, sulfonate, NE$^1$E$^2$, alkylene-NE$^1$E$^2$, trifluoromethyl, nitro, alkoxycarbonyl, carboxyl or cyano.

6. A compound as claimed in claims 3, wherein R$^6$ and R$^7$ together form a moiety of formulae II.5 to II.9:

(II.5)

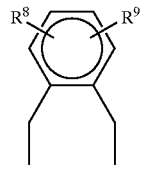

(II.6)

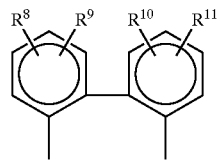

(II.7)

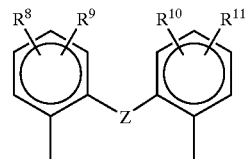

(II.8)

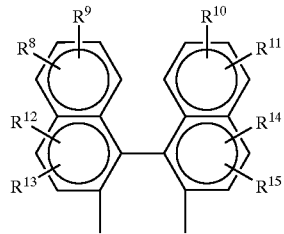

-continued (II.9)

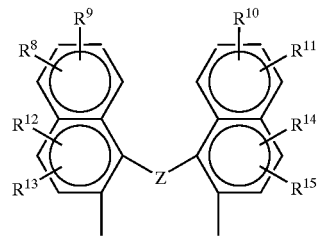

wherein

Z is O, S or NR$^{16}$, where R$^{16}$ is alkyl, cycloalkyl or aryl, or

Z is a C$_1$–C$_3$-alkylene bridge which optionally meets one or both of the following requirements (a) and (b):
(a) the bridge has a double bond,
(b) the bridge carries an alkyl, cycloalkyl or aryl substituent, where the aryl substituent is optionally substituted by one, two or three substituents selected from a group consisting of alkyl, alkoxy, halogen, SO$_3$H, sulfonate, NE$^1$E$^2$, alkylene-NE$^1$E$^2$, trifluoromethyl, nitro, alkoxycarbonyl and cyano, or Z is a C$_2$–C$_3$-alkylene bridge which is interrupted by O, S or NR$^{16}$, R$^8$, R$^9$, R$^{10}$, R$^{11}$, R$^{12}$, R$^{13}$, R$^{14}$ and R$^{15}$ are each, independently of one another, hydrogen, alkyl, cycloalkyl, aryl, alkoxy, halogen, SO$_3$H, sulfonate, NE$^1$E$^2$, alkylene-NE$^1$E$^2$, trifluoromethyl, nitro, alkoxycarbonyl, carboxyl or cyano.

7. A compound as claimed in claim 1 which is selected from a group consisting of compounds of formulae I.i to I.v (I.i)

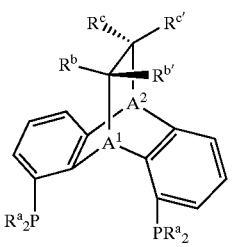

(I.ii)

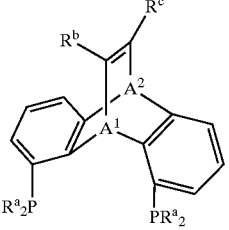

(I.iii)

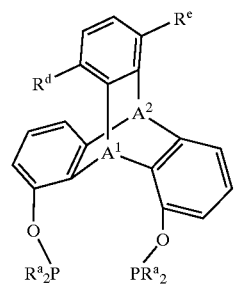

-continued (I.iv)

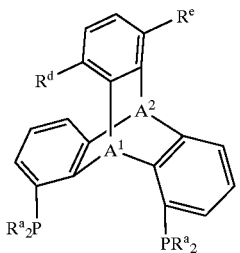

(I.v)

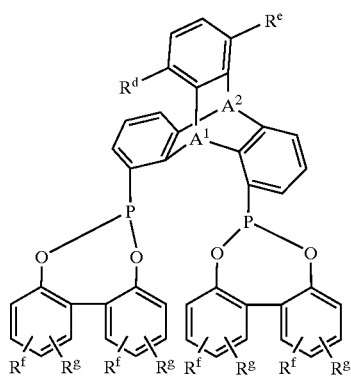

where

Rᵃ is selected from a group consisting of $C_1$–$C_6$-alkyl, $C_1$–$C_6$-alkoxy, $C_5$–$C_7$-cycloalkoxy, phenyl, phenoxy and pentafluorophenyl, where the phenyl- and phenoxy groups optionally carry a substituent selected from a group consisting of carboxyl, carboxylate, —SO₃H and sulfonate, Rᵇ, Rᵇ', Rᶜ and Rᶜ' are selected independently from a group consisting of hydrogen, $C_1$–$C_6$-alkyl, $C_1$–$C_6$-alkoxy, $C_1$–$C_6$-alkoxycarbonyl and aryl, Rᵈ and Rᵉ are selected independently from a group consisting of hydrogen and $C_1$–$C_6$-alkyl, Rᶠ and Rᵍ are selected independently from a group consisting of hydrogen, $C_1$–$C_6$-alkyl and $C_1$–$C_6$-alkoxy, and $A^1$ and $A^2$ are each, independently of one another, N or $CR^5$, where $R^5$ is hydrogen or $C_1$–$C_8$-alkyl.

8. A process for preparing a compound of the formula I in which X is a moiety of formulae II.1, II.2, II.3 or II.4

(II.1)

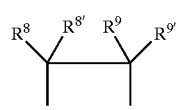

(II.2)

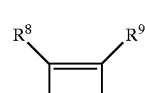

(II.3)

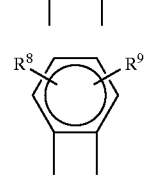

-continued (II.4)

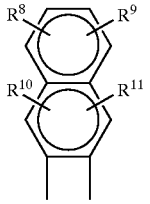

where $R^8$, $R^{8'}$, $R^9$, $R^{9'}$, $R^{10}$ and $R^{11}$ are each, independently of one another, hydrogen, alkyl, cycloalkyl, aryl, alkoxy, halogen, SO₃H, sulfonate, $NE^1E^2$, alkylene-$NE^1E^2$, trifluoromethyl, nitro, alkoxycarbonyl, carboxyl or cyano, which comprises reacting a compound of formula I.1

(I.1)

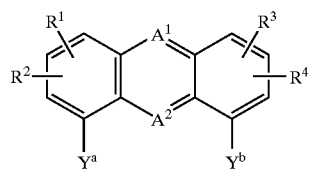

where $A^1$ and $A^2$ are each, independently of one another, B, N, P or $CR^5$, where $R^5$ is hydrogen, alkyl, cycloalkyl, aryl, heteroaryl or a polymeric support which is optionally bound via a spacer group, $Y^a$ and $Y^b$ are each, independently of one another, a group $Y^1$ or $Y^2$ or $Y^a$ and $Y^b$ are each, independently of one another, halogen, OH, OC(O)CF₃ or SO₃Me where Me=hydrogen, Li, Na or K, and $Y^a$ and/or $Y^b$ are additionally hydrogen when the phenyl ring to which they are bonded carries an alkoxy group which is located in ortho position of $Y^a$ and/or $Y^b$, and $R^1$, $R^2$, $R^3$ and $R^4$ are each, independently of one another, hydrogen, alkyl, cycloalkyl, aryl, alkoxy, halogen, SO₃H, sulfonate, $NE^1E^2$, alkylene-$NE^1E^2$, trifluoromethyl, nitro, alkoxycarbonyl or cyano, with a compound of formula II.a, II.b, II.c or II.d (II.a)

$$R^8—C≡C—R^9$$

(II.b)

$$R^8R^{8'}C=CR^9R^{9'}$$

(II.c)

(II.d)

or a precursor of a compound of the formula II.c or II.d in a [4+2]-Diels-Alder cycloaddition, and optionally functionalizing one or both of $Y^a$ and $Y^b$ to form the groups $Y^1$ and $Y^2$.

9. A catalyst comprising at least one complex of a metal of transition group VIII and at least one ligand selected from the compounds of formula I as defined in claim 1.

10. A catalyst as claimed in claim 9, wherein the metal of transition group VIII is selected from cobalt, ruthenium, iridium, rhodium, nickel, palladium and platinum.

11. A catalyst as claimed in claim 9 which further comprises at least one additional ligand selected from halides, amines, carboxylates, acetylacetonate, arylsulfonates and alkylsulfonates, hydride, CO, olef ins, dienes, cycloolef ins, nitriles, N-containing heterocycles, aromatics and heteroaromatics, ethers, $PF_3$, phospholes, phosphabenzenes and monodentate, bidentate and polydentate phosphine, phosphinite, phosphonite, phosphoramidite and phosphite ligands.

12. A process for the hydroformylation or carbonylation of a compound containing at least one ethylenically unsaturated double bond, which comprises reacting the compound with carbon monoxide, hydrogen and optionally a compound which contains a nucleophilic group in the presence of the catalyst defined in claim 9.

13. A process as claimed in claim 12, which further comprises preparing the catalyst in situ by reacting at least one compound of the formula I, a compound or complex of a metal of transition group VIII and optionally an activating agent in an inert solvent under the conditions for hydroformylation or carbonylation.

14. The compound of formula I defined in claim 1, wherein $A^1$ and $A^2$ are independently selected from the group of N and $CR^5$, wherein $R^5$ is hydrogen or $C_1$–$C_8$-alkyl.

15. The compound of formula I defined in claim 1, wherein each of $Y^1$ and $Y^2$ represents, independently of the other, a group containing a phosphorus atom which is bound directly or via an oxygen atom to the phenyl ring.

16. The catalyst defined in claim 9, wherein X of the ligand compound of formula I is a $C_1$–$C_{10}$-alkylene bridge which optionally meets one or more of the following requirements (a) to (d):

(a) the bridge has one, two, three or four double bonds, (b) the bridge carries one, two, three or four substituents selected from a group consisting of:
alkyl, alkoxy, halogen, nitro, cyano, carboxyl, carboxylate, cycloalkyl and aryl, where the aryl substituent is optionally substituted by one, two or three substituents selected from a group consisting of alkyl, alkoxy, halogen, $SO_3H$, sulfonate, $NE^1E^2$, alkylene-$NE^1E^2$, trifluoromethyl, nitro, alkoxycarbonyl and cyano, (c) the bridge is interrupted by one, two or three nonadjacent, substituted or unsubstituted heteroatoms, (d) the bridge is fused with one, two or three rings selected from aryl and heteroaryl rings, where the fused-on rings optionally carry one, two or three substituents selected from a group consisting of:
alkyl, cycloalkyl, aryl, alkoxy, cycloalkoxy, aryloxy, acyl, halogen, $SO_3H$, sulfonate, trifluoromethyl, nitro, cyano, carboxyl, alkoxycarbonyl, $NE^1E^2$ and alkylene-$NE^1E^2$.

17. The catalyst defined in claim 9, wherein $A^1$ and $A^2$ of the ligand compound of formula I are independently selected from the group of N and $CR^5$, wherein $R^5$ is hydrogen or $C_1$–$C_8$-alkyl.

18. The catalyst defined in claim 9, wherein each of $Y^1$ and $Y^2$ of the ligand compound of formula I represents, independently of the other, a group containing a phosphorus atom which is bound directly or via an oxygen atom to the phenyl ring.

* * * * *